United States Patent

Spivack

[11] 4,233,208
[45] Nov. 11, 1980

[54] POLYMER COMPOSITIONS STABILIZED WITH HINDERED PHENYL SECONDARY PHOSPHITES

[75] Inventor: John D. Spivack, Spring Valley, N.Y.

[73] Assignee: Ciba-Geigy Corporation, Ardsley, N.Y.

[21] Appl. No.: 923,836

[22] Filed: Jul. 12, 1978

Related U.S. Application Data

[63] Continuation of Ser. No. 661,585, Feb. 26, 1976, abandoned.

[51] Int. Cl.$^3$ .......................... C08K 5/51; C08K 5/52
[52] U.S. Cl. .................... 260/45.8 NT; 260/45.7 PH; 260/45.85 B; 260/45.85 S; 260/45.9 NC; 260/45.95 D; 260/45.95 H
[58] Field of Search ................. 260/45.7 PH, 45.85 S, 260/45.8 NT

[56] References Cited

U.S. PATENT DOCUMENTS

| | | | |
|---|---|---|---|
| 2,437,046 | 3/1948 | Rothrock, Jr. et al. | 260/45.7 PH |
| 3,115,465 | 12/1963 | Orloff et al. | 260/45.7 PH |
| 3,188,298 | 6/1965 | Williamson et al. | 260/45.95F |
| 3,206,431 | 9/1965 | Doyle et al. | 106/182 |
| 3,281,506 | 10/1966 | Shepard et al. | 260/960 |
| 3,301,816 | 1/1967 | Burgess | 260/45.95 F |
| 3,425,987 | 2/1969 | Oswald et al. | 260/45.7 PH |
| 3,487,044 | 12/1969 | Tholstrup | 260/45.85 S |
| 3,636,031 | 1/1972 | Drake et al. | 260/45.8 NT |
| 3,637,555 | 1/1972 | Marinacci et al. | 260/45.85 S |
| 3,781,242 | 12/1973 | Mathis et al. | 260/45.8 NT |

FOREIGN PATENT DOCUMENTS

763491 7/1967 Canada .

Primary Examiner—Howard E. Schain
Assistant Examiner—R. A. White
Attorney, Agent, or Firm—Harry Falber

[57] ABSTRACT

Organic polymeric materials normally subject to oxidative and ultraviolet light deterioration are stabilized by incorporating therein a compound of the formula

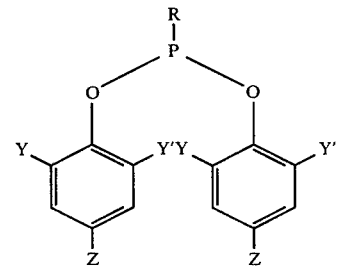

wherein R is hydroxyl or chlorine, Y and Y' are independently alkyl, aralkyl or halogen, and Z is independently hydrogen, halogen, alkyl or aralkyl.

26 Claims, No Drawings

POLYMER COMPOSITIONS STABILIZED WITH HINDERED PHENYL SECONDARY PHOSPHITES

This is a continuation of application Ser. No. 661,585 filed on Feb. 26, 1976, now abandoned.

BACKGROUND OF THE INVENTION

Most organic polymers, especially polyolefins such as polyethylene or polypropylene, which are used for manufacturing articles tend to develop color with passage of time. The discoloration may be due to various factors such as the decomposition of the polymer, the antioxidant or to the presence of residual metal catalyst or residual peroxides used to control polymerization. It may also be due to the basic nature of polymeric material, the additives used in the polymeric material or the effect of heat on the polymeric material. The development of color is undesirable because it indicates polymer degradation and results in further reduction of the quality of the polymer. Thus, one of the objects of this invention is to provide a stabilized composition which would improve the quality of polymers by preventing the discoloration of the polymer.

The prior art discloses many materials which inhibit the discoloration of polymers on exposure to heat and light. It is well known to stabilize polyolefins and styrenic polymers by the use of phosphites. Thus, for example, phosphites can be used in conjunction with UV absorbers such as benzophenones and benzotriazoles to achieve improved stabilization of polypropylene on outdoor exposure to sunlight. However, a phosphite is generally not used as the sole light stabilizer in polypropylene because of its limited effectiveness. Unexpectedly, it has been found that the phosphites of this invention can be used effectively in polymers, such as polypropylene, as the sole light stabilizer. Furthermore, it has also been surprisingly found that these phosphites act as effective antioxidants for polymers, both when used alone and in combination with thiosynergists.

It is also well known in the art to use phosphites in conjunction with hindered phenols as stabilizers for unsaturated elastomers. A notable example of a phosphite widely used in such a combination is trinonylphenyl phosphite (TNPP). It has now been found that the phosphites of this invention are surprisingly much more effective color stabilizers and antioxidants than trinonylphenyl phosphite.

DETAILED DISCLOSURE

This invention accordingly relates to compositions comprising organic materials stabilized with compounds having the formula

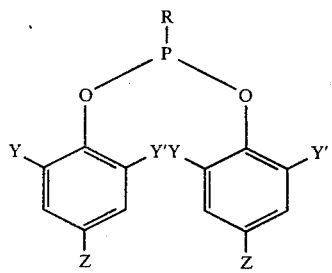

wherein
R is hydroxyl or chlorine, preferably hydroxyl,

Y and Y' are independently alkyl having from 1 to 12, especially 3 to 12 carbon atoms, aralkyl having from 7 to 12 carbon atoms or halogen, preferably chlorine and bromine, and Z is independently hydrogen, halogen, alkyl having from 1 to 12 carbon atoms or aralkyl having from 7 to 12 carbon atoms.

Y and Y' can be straight- or branched-chain alkyl having from 1 to 12, especially 3 to 12, carbon atoms. Examples of Y and Y' are 1,1-dimethylpropyl, 1,1,3,3-tetramethylbutyl, 1,1,2-trimethylpropyl, isopropyl, tert-butyl, 1,1-dimethylbutyl, nonyl, and dodecyl. Preferably, Y and Y' are isopropyl and tert-butyl groups, most preferably tert-butyl groups.

Y and Y' can be aralkyl having from 7 to 12 carbon atoms. One or two alkyl substituents may be present on the aromatic ring of the aralkyl group. Examples of such aralkyl groups are benzyl, phenylethyl, phenylpropyl, p-methylbenzyl, phenylhexyl, 3,5-dimethylbenzyl, α,α-dimethylbenzyl, and α,p-dimethylbenzyl.

Z can be hydrogen, halogen, preferably hydrogen and chlorine, alkyl having from 1 to 12 carbon atoms, preferably methyl, isopropyl, tert-butyl and nonyl, or aralkyl having from 7 to 12 carbon atoms, preferably benzyl, phenylethyl and phenylpropyl.

Z can be straight- or branched-chain alkyl having from 1 to 12 carbon atoms. Examples are methyl, isopropyl, tert-butyl, nonyl and dodecyl. Preferably, Z is methyl or tert-butyl.

Z can be aralkyl having from 7 to 12 carbon atoms. One or two alkyl substituents may be present on the aromatic ring of the aralkyl group. Examples are benzyl, phenylethyl, phenylpropyl, p-methylbenzyl, α-p-dimethylbenzyl, phenylhexyl, 3,5-dimethylbenzyl, and α,α-dimethylbenzyl.

It is understood that although R has been defined as OH, compounds of formula I consist of 2 tautomers in equilibrium with one another:

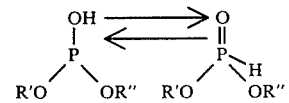

where R' and R" represent

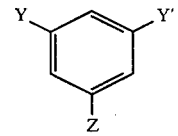

The compositions of matter of this invention which are stabilized against deterioration comprise a polymer normally subject to deterioration containing from about 0.005% to 5% by weight of the polymer of the compounds of formula I. Organic materials such as, for example, the following polymers, can be stabilized using the compounds of the formula I.

1. Polymers which are derived from hydrocarbons with single or double unsaturation, such as polyolefins, for example, polyethylene which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylene-propylene copolymers, propylene-butene-1 copolymers, propyleneisobutylene copolymers, styrene-butadiene copolymers and terpolymers of ethylene and propylene with a diene, such as, for example, hexadiene, dicyclopentadiene or ethylidene-norbornene; mixtures of above mentioned homopolymers, such as for example, mixtures of polypropylene and polyethylene, polypropylene and polybutene-1, or polypropylene and polyisobutylene.

2. Vinyl polymers containing halogen, such as polyvinyl chloride, polyvinylidene chloride, polyvinyl fluoride, but also polychloroprene and chlorinated rubbers.

3. Polymers which are derived from $\alpha,\beta$-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.

8. Polyurethanes and polyureas.

9. Polycarbonates.

10. Polysulphones.

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate or poly-14-dimethylol-cyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as cross-linking agents, and also their halogen-containing modifications of low inflammability.

16. Natural polymers such as cellulose, rubber, proteins and their polymer-homologously chemically modified derivatives, such as cellulose acetates, cellulose propionates and cellulose butyrates, or the cellulose ethers, such as methylcellulose.

17. High molecular monomeric substances, for example, mineral oils, animal and vegetable fats, oils and waxes, or oils, waxes and fats based on synthetic esters.

The compounds of this invention are paticularly useful as UV light stabilizers, especially for the protection of polyolefins, for instance, polyethylene, polypropylene, poly(butene-1), poly(pentene-1), poly(3-methylbutene-1), poly (4-methylpentene-1), various ethylene-propylene copolymers and the like.

Other substrates in which the compounds of this invention are particularly useful are polystyrene, including impact polystyrene, ABS resin, SBR, isoprene, as well as natural rubber, polyesters including polyethylene terephthalate and polybutylene terephthalate, including copolymers.

In general, the stabilizers of this invention are employed from about 0.01 to about 5% by weight of the stabilized composition, although this will vary with the particular substrate and application. An advantageous range is from about 0.05 to about 2%, and especially 0.1 to about 1%.

For addition to polymeric substrates, the stabilizers can be blended before polymerization or after polymerization, during the usual processing operations, for example, by hot-milling, the composition then being extruded, pressed, blow-molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface or films, fabrics, filaments or the like to provide effective stabilization. Where the polymer is prepared from a liquid monomer as in the case of styrene, the stabilizer may be dispersed or dissolved in the monomer prior to polymerization or curing.

In the case of crosslinked polyethylene, the compounds are added before the crosslinking.

The following may be mentioned as examples of further additives with which the compounds of the formula I can be co-employed:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol, 2,6-dioctadecyl-4-methylphenol, 1.2 Derivative of alkylated hydroquinones, such as, for example, 2,5-di-tert.-butyl-hydroquinone, 2,5-di-tert.-amylhydroquinone, 2,6-di-tert.-butylhydroquinone, 2,5-di-tert.-butyl-4-hydroxy-anisole, 3,5-di-tert.-butyl-4-hydroxyanisole, tris-(3,5-di-tert.-butyl-4-hydroxyphenyl)-phosphite, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'- methylene-bis-(6-tert.-butyl-2-methylphenol), 4,4'-methylene-bis-(2,6'-di-tert.-butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)butane, 1,1-bis-(5-tert.-butyl-4-hydroxy-2-methylphenyl)-butane, 2,2-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].

1.5 O-, N- and S-benzyl compounds, such as, for example, 3,5,3',5'-tetra-tert.-butyl-4,4'-dihydroxydibenzyl ether, 4-hydroxy-3,5-dimethylbenzyl-mercaptoacetic acid octadecyl ester, tris(3,5-di-tert.-butyl-4-hydroxybenzyl)-amine and bis-(4-tert.-butyl-3-hydroxy-2,6-dimethylbenzyl)-dithioterephthalate.

1.6 Hydroxybenzylated malonic esters, such as, for example, 2,2-bis-(3,5-di-tert.-butyl-2-hydroxybenzyl)-malonic acid dioctadecyl ester, 2-(3-tert.-butyl-4-hydroxy-5-methylbenzyl)-malonic acid dioctadecyl ester, 2,2-bis-(3,5-di-tert.-butyl-4-hydroxybenzyl)-malonic acid didodecylmercaptoethyl-ester and 2,2-bis-(3,5-di-tert.-butyl-4-hydroxybenzyl)-malonic acid di-[4-(1,1,3,3-tetramethylbutyl)-phenyl]-ester.

1.7 Hydroxybenzyl-aromatics, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example, 2,4-bis-octylmercapto-6-(3,5,di-tert.-butyl-4-hydroxy-anilino)-s-triazine, 2-octylmercapto-4,6-bis-(3,5-di-tert-butyl-4-hydroxy-anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxy-phenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)-isocyanurate.

1.9 Amides of β-(3,5-di-tert.-butyl-4-hydroxyphenyl)-propionic acid, such as, for example, 1,3,5-tris-(3,5-di-tert.butyl-4-hydroxyphenyl-propionyl-hexahydro-s-triazine and N,N'-di-(3,5-di-tert.-butyl-4-hydroxyphenyl-propionyl)-hexamethylenediamine.

1.10 Esters of β-(3,5-di-tert.-butyl-4-hydroxyphenyl-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, trishydroxyethyl isocyanurate and 4-hydroxymethyl-1-phospha-2,6,7-trioxabicyclo[2,2,2]-octane.

1.11 Esters of β-(5-tert.-butyl-4-hydroxy-3-methylphenyl propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3,thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.12 Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethyl hexanediol, trimethylolethane, treimethylolpropane, tris-hydroxyethyl isocyanurate and 4-hydroxymethyl-1-phospha-2,6,7-trioxabicyclo[2,2,2]octane.

1.13 Acylaminophenols, such as, for example, N-(3,5-di-tert.-butyl-4-hydroxyphenyl)stearic acid amide, N,N'-di-(3,5-di-tert-butyl-4-hydroxyphenyl)-thiobis-acetamide and thiophosphoric acid O,O-diethyl ester 3,5-di-tert.-butyl-4-hydroxy anilide.

1.14 Benzylphosphonates, such as, for example, 3,5-di-tert.-butyl-4-hydroxybenzyl-phosphonic acid dimethyl ester, 3,5-di-tert.-butyl-4-hydroxybenzyl-phosphonic acid diethyl ester, 3,5-di-tert.-butyl-4-hydroxybenzyl-phosphonic acid dioctadecyl ester and 5-tert.-butyl-4-hydroxy-3-methylbenzyl-phosphonic acid diotadecyl ester.

1.15 Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.-butyl-p-phenylenediamine, 6-ethoxy-2-2,4-trimethyl-1,2-dihydroquinoline, 6-dodecyl-2,2,4-trimethyl-1,2-dihydroquinoline, monoocylyiminodibenzyl and dioctyliminodibenzyl and polymerised 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec.-octyl-p-phenylenediamine, N-phenyl-N'sec.-octyl-p-phenylenediamine, N,N'-di-(1,4-dimethylpentyl)-p-phenylenediamine, N,N'-dimethyl-N,N'di-(sec.-octyl)-p-phenylenediamine, 2,6-dimethyl-4-methoxyaniline, 4-ethoxy-N-sec.-butylaniline, the condensation product of diphenylamine and acetone, aldol-1-naphthylamine and phenothiazine.

2. UV absorbers and light stabilizers 2.1 2-(2'-Hydroxyphenyl)-benztriazoles, such as, for example, the 5'-methyl-, 3'5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl', 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl- derivative.

2.2 2,4-Bis-(2'-hydroxyphenyl)-6-alkyl-s-triazines, such as, for example, the 6-ethyl-, 6-heptadecyl, or 6-undecylderivative.

2.3 2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy-derivative.

2.4 1,3-Bis-(2'-hydroxy-benzoyl)-benzenes, such as for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5 Esters of optionally substituted benzoic acids, such as, for example, phenyl salicylate, octylphenyl salicylate, dibenzoylresorcinol, bis-(4-tert.-butylbenzoyl)-resorcinol, benzoyl-resorcinol and 3,5-di-tert.-butyl-4-hydroxybenzoic acid 2,4-di-tert.-butyl-phenyl ester, octadecyl ester or 2-methyl-4,6-di-tert.-butyl-phenyl ester.

2.6 Acrylates, such as, for example, α-cyano-β,β-diphenylacrylic acid ethyl ester or isooctyl ester, α-carbomethoxycinnamic acid methyl ester, α-cyano-β-methyl-p-methoxycinnamic acid methyl ester or butyl ester and N-(β-carbomethoxy-vinyl)-2methyl-indoline.

2.7 Nickel compounds, such as, for example, nickel complexes of 2,2′-thio-bis-[4-(1,1,3,3-tetramethyl-butyl)-phenol], such as the 1:1 or 1:2 complex, optionally with additional ligands such as n-butylamine, triethanolamine or N-cyclohexyl-di-ethanolamine, nickel complexes of bis-[2-hydroxy-4-(1,1,3,3-tetramethylbutyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert-butylbenzyl-phosphonic acid monoalkyl esters, such as of the methyl, ethyl or butyl ester, nickel complex of ketoximes such as of 2-hydroxy-4-methyl-phenyl undecyl ketonoxime, nickel 3,5-di-tert.-butyl-4-hydroxybenzoate and nickel isopropylxanthate.

2.8 Oxalic acid diamides, such as, for example, 4,4′-di-octyl-oxy-oxanilide, 2,2′-di-octyloxy-5,5′-di-tert.-butyl-oxanilide, 2,2′-di-dodecyloxy-5,5′-di-tert.-butyl-oxanilide 2-ethoxy-2′-ethyl-oxanilide, N,N′-bis-(3-dimethylaminopropyl)-oxalamide, 2-ethoxy-5-tert.-butyl-2′-ethyl-oxanilide and its mixture with 2-ethoxy-2′-ethyl-5,4′-di-tert.-butyl-oxanilide and mixtures of ortho- and para-methoxy- as well as of o- and p-ethoxy-disubstituted oxanilides, 3. Metal deactivators, such as, for example, oxanilide, isophthalic acid dihydrazide, sebacic acid bis-phenyl-hydrazide, bis-benzylidene-oxalic acid dihydrazide, N,N′-diacetyl-adipic acid dihydrazide, N,N′-bis-salicyloyloxalic oxalic acid dihydrazide, N,N′-bis-salicyloyl-hydrazine, N,N′-bis-(3,5-di-tert.-butyl-4-hydroxyphenyl-propionyl)-hydrazine, N-salicyloyl-N′-salicylal-hydrazine, 3-salicyloylamino-1,2,4-triazole and N,N′-bis-salicyloyl-thiopropionic acid dihydrazide.

4. Compounds which destroy peroxide, such as, for example, esters of β-thiodipropionic acid, for example the lauryl, stearyl, myristyl or tridecyl esters, mercapto-benzimidazole or the zinc salt of 2-mercapto-benzimidazole.

5. Polyamide stabilizers, such as, for example, copper salts in combination with iodides and/or phosphorus compounds and salts of divalent manganese.

6. Basic co-stabilizers, such as, for example, melamine, benzoquanamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, Zn stearate, Mg stearate Na ricinoleate and K palmitate, antimony pyrocatechloate or zinc pyrocatecholate.

7. PVC stabilizers, such as, for example, organic tin compounds, organic lead compounds and barium-cadmium salts of fatty acids.

8. Nucleating agents, such as, for example, 4-tert. butyl-benzoic acid, adipic acid and diphenylacetic acid.

9. Urea derivatives, such as, for example, N-cyclohexyl-N′-1-naphthylurea, N-phenyl-N,N′-dicyclohexylura, N-phenyl-N′-2-naphthylurea, N-phenylthiourea and N,N′-dibutylthiourea.

10. Other additives, such as, for example, plasticizers, lubricants, emulsifiers, fillers, carbon black, asbestos, kaolin, talc, glass fibres, pigments, optical brighteners, flameproofing agents, antistatic agents, pourpoint depressants, corrosion and rust inhibitors, dispersing agents, demulsifiers, antifoaming agents, accelerators and the other chemicals used in rubber compounding, dyes, pigments, metal chelating agents, dyesites and the like.

The hindered phosphites are particularly useful in stabilizing polymer systems containing reinforcing agents and flame retardants, e.g., the compounds of this invention help to stabilize polyesters, e.g., polybutylene terephthalate containing fiber glass and also polyesters containing flame-retardants, e.g., polyethylene or polybutylene terephthalate containing halogenated (e.g., brominated) aryl flame-retardants.

The hindered phosphites of this invention are particularly useful in preventing discoloration due to processing as well as thermal aging and light exposure of polymer compositions containing polyarcylonitrile and polymethacrylonitrile resins. For example, a rubber modified polyacrylonitrile used for beverage bottles is inhibited from discoloration when a hindered phosphite of this invention is included in the formulation.

Often combinations such as these, particularly the sulfur-containing esters (Section 4, page 18), and/or the ultraviolet light stabilizers (Section 2, pages 15-17), will produce superior results in certain applications to those expected from the properties of the individual components.

The following formula represents co-stabilizers which are in certain instances very useful in combination with the stabilizers of this invention:

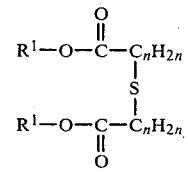

wherein $R^1$ is an alkyl group having from 6 to 24 carbon atoms, and n is an integer from 1 to 6. Especially useful compounds of this type are dilauryl-β-thiodipropionate (DLTDP), distearyl-β-thiodipropionate (DSTDP), and dimyristyl-β-thiodipropionate. The above co-stabilizers are used in the amount of from 0.005 to 5% by weight of the organic material, and preferably from 0.1 to 1%.

Another co-stabilizer found to be very effective in combination with the stabilizers of this invention has the formula

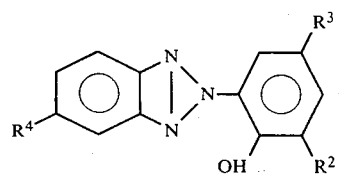

wherein
$R^2$ is hydrogen, chlorine or lower alkyl containing from 1 to 6 carbon atoms,
wherein
$R^2$ is hydrogen, chlorine or lower alkyl containing from 1 to 6 carbon atoms, R³ is hydrogen, alkyl containing 1 to 12 carbon atoms, phenyl or benzyl, and R⁴ is hydrogen, chlorine or (lower) alkyl containing from 1 to 6 carbon atoms.

In a preferred embodiment, R⁴ is hydrogen, chlorine or a methyl group; R² is hydrogen, chlorine, t-butyl, t-amyl; and R³ is alkyl of from 1 to 12 carbon atoms such as methyl, ethyl, hexyl, octyl, dodecyl, t-butyl, t-amyl, isopropyl and the like.

The above benzotriazoles are added to the polymer substrate in an amount of from about 0.005% to about 5% by weight based on the weight of the polymer and more preferably from 0.05% to 2%.

Although the compounds of this invention are to some degree also effective as thermal stabilizers, if the processing of the polymer is carried out at high temperatures it is advantageous to incorporate additional antioxidants.

In most applications, it is desirable to incorporate into the resins composition, sufficient thermal antioxidants to protect the plastic against thermal and oxidative degradation. The amount of antioxidant required will be comparable to that of the actinic stabilizer. Namely, from about 0.005% to 5% and preferably from 0.01% to 2% by weight.

The best results have been obtained with the preferred class of thermal antioxidants, the hindered phenols. These compounds have been found to provide the best thermal stabilization with the lease discoloration in the compositions of the invention. Among the preferred class of thermal antioxidants may be mentioned the following:
di-n-octadecyl(3,5-di-butyl-4-hydroxybenzyl)malonate
2,6-di-t-butylphenol
2,2'-methylene-bis(6-butyl-4-methylphenol)
2,6-di-t-butylhydroquinone
octadecyl-(3,5-di-t-butyl-4-hydroxybenzylthio) acetate
1,1,3-tris(3-t-butyl-6-methyl-4-hydroxyphenyl) butane
1,4-bis(3,5-di-t-butyl-4-hydroxybenzyl)-2,3-5,6-tetramethylbenzene
2,4-bis-(3,5-di-t-butyl-4-hydroxyphenoxy)-6-(n-octylthio)-1,3,5-triazine
2,4-bis-(4-hydroxy-3,5-di-t-butylphenoxy)-6-(n-octylthioethylthio)-1,3,5-triazine
2,4-bis-(n-octylthio)-6-(3,5-di-t-butyl-4-hydroxyanilino)-1,3,5-triazine
2,4,6-tris-(4-hydroxy-3,5-di-t-butylphenoxy)-1,3,5-triazine
n-octadecyl-β-(3,5-di-t-butyl-4-hydroxyphenyl) propionate
2,4,6-tris(3,5-di-tert-butyl-4-hydroxybenzyl)-isocyanurate
di-n-dodecyl-6-tert-butyl-2,3-dimethyl-4-hydroxybenzyl phosphonate
stearamido N,N-bis-[ethylene 3-(3,5-di-t-butyl-4-hydroxyphenyl)propionate]
1,2-propylene glycol bis[3-(3,5-di-t-butyl-4-hydroxyphenyl)propionate]
pentaerythritol tetrakis-[3-(3,5-di-t-butyl-4-hydroxyphenyl)propionate]
dioctadecyl-3,5-di-t-butyl-4-hydroxybenzylphosphonate
di-n-octadecyl-1-(3,5-di-t-butyl-4-hydroxyphenyl)-ethanephosphonate The above phenolic hydrocarbon stabilizers are known and many are commercially available.

The above exemplified antioxidants and other related antioxidants which are incorporated herein by reference, are disclosed in greater detail in the following patents:
Netherlands Patent Specification No. 67/1119, issued Feb. 19, 1968; Netherlands Patent Specification No. 68/03498, issued Sept. 18, 1968; U.S. Pat. Nos. 3,255,191; 3,330,859; 3,644,482; 3,281,505; 3,531,483; 3,285,855; 3,364,250; 3,368,997; 3,357,944 and 3,758,549.

The compounds of this invention are generally prepared according to procedures described in U.S. Pat. No. 3,281,506. This patent, however, does not disclose the preparation or properties of bis-(2,4,6-tri-t-butylphenyl) phosphite. In the present work, this compound could not be made by the alkaline hydrolysis process disclosed in the above patent. Instead, bis-(2,4,6-tri-t-butylphenyl)phosphite was successfully prepared from the chloridite by treatment with alcohols such as, methanol, ethanol and butanol.

In particularly advantageous embodiment of the invention, the hindered phosphites are employed in combination with p-hydroxybenzoates having the general formula

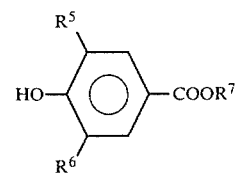

II wherein

R⁵ is (lower) alkyl containing from 1 to 6 carbon atoms,

R⁶ is hydrogen or (lower) alkyl containing from 1 to 6 carbon atoms, and

R⁷ is alkyl or alkenyl of from 1 to 24 carbon atoms, preferably alkyl of from 1 to 24 carbon atoms, phenyl, lower alkyl substituted phenyl, benzyl or lower alkyl substituted benzyl groups, such that no more than two lower alkyl substituents are present in said phenyl or benzyl groups. Preferred among the above phenyl and benzyl groups defining R⁷ are phenyl and phenyl substituted by one or two alkyl groups of 1 to 12 carbon atoms.

In a preferred embodiment, R⁵ and R⁶ are t-butyl or t-amyl groups and R⁷ is a di(lower alkyl) phenol. Illustrative examples of hydroxybenzoates are given below:
(2',4'-di-t-butylphenyl)-3,5-di-t-butyl-4-hydroxybenzoate
methyl-3-methyl-5-isopropyl-4-hydroxybenzoate
ethyl-3,5-diisopropyl-4-hydroxybenzoate
propyl-3,5-di-sec-butyl-4-hydroxybenzoate
isobutyl-3,5-di-tert-amyl-4-hydroxybenzoate
decyl-3,5-di-tert-octyl-4-hydroxybenzoate
cyclohexyl-3,5-di-tert-amyl-4-hydroxybenzoate
dodecyl-3-methyl-5-isoamyl-4-hydroxybenzoate
octadecyl-3,5-diisopropyl-4-hydroxybenzoate
hexadecyl-3,5-di-tert-butyl-4-hydroxybenzoate
3-fluoropropyl-3,5-di-tert-amyl-4-hydroxybenzoate
allyl-3,5-di-tert-butyl-4-hydroxybenzoate
2-butenyl-3,5-diisopropyl-4-hydroxybenzoate
oleyl-5-methyl-5-tert-amyl-4-hydroxybenzoate
phenyl-3,5-diisopropyl-4-hydroxybenzoate
p-t-octylphenyl-3,5-di-tert-amyl-4-hydroxybenzoate
(2',4'-dimethylphenyl)-3,5-di-tert-octyl-4-hydroxybenzoate p-isopropylphenyl-3-methyl-5-tert-amyl-4-hydroxybenzoate
naphthyl-3,5-di-tert-butyl-4-hydroxybenzoate
6-methylnaphthyl-3,5-di-tert-hexyl-4-hydroxybenzoate
p-chlorophenyl-3,5-di-tert-butyl-4-hydroxybenzoate
2,4-dibromophenyl-3,5-diisopropyl-4-hydroxybenzoate The p-hydroxybenzoate light stabilizers of Formula II are added to the polymer substrate in an amount of from about 0.005% to 5% by weight based on the weight of polymer, and more preferably from 0.05% to 2%.

The following examples, presented for illustration and not limitation, will further serve to typify the nature of the present invention.

EXAMPLE 1

Bis(2,4,6-tri-tert.-butylphenyl)phosphite

To 58.9 grams of bis(2,4,6-tri-tert-butylphenyl) phosphorochloridite, (0.10 moles), dissolved in 120 ml. of toluene at 55°, was added 60 ml. of methanol, the reaction mixture being heated at 64° C. for 19 hours. The reaction product was isolated by evaporation of the solvent and retreated product showed a negative test for halogen. The crude product was isolated by evaporation of the solvent at reduced pressure. The residual product was purified by trituration with 100 ml. of ethyl acetate followed by crystallization from the same solvent, yielding white crystals melting at 239°–244° C.

| Analysis: | % C | % H |
| --- | --- | --- |
| Calculated | 75.75 | 10.42 |
| Found | 75.89 | 10.44 |

EXAMPLE 2

Outdoor Exposure Tests

The indicated amounts of additives (Table I) were solvent blended onto polypropylene powder (Hercules Profax 6501), the powder was agitated for 5 minutes in a Kitchen Aid planetary mixer and the powder mixture was dried in a vacuum oven at a vacuum of 30 inches of water overnight.

The polypropylene powder containing the additives was extruder compounded at 232° C. into pellets, and the pellets were melt spun at 260° C. into 5 mil monofilaments. The filaments were air cooled and oriented at a 4:1 ratio between hot (125° C.) and cold godets and wound onto a fiber spool. The filament was mounted on wooden exposure frames and exposed at 45° south direct weathering inland in Puerto Rico. Samples were removed from exposure periodically and tensile tested on the Instron Table Model tensile tester using fiber grips.

The results indicated below show the Kilolangleys of Puerto Rico Exposure to 50 percent retention of tensile strength. A Langley is a measure of energy in the ultraviolet region to which the samples have been exposed.

The amounts of the additives are expressed in weight percent based on the weight of the polymer.

TABLE I

Puerto Rico Exposure
Eilolangieys of Puerto Rico Exposure
to 50 Percent Retention of Tensile Strength

| 5 Mil Monofilaments Formulation | Kilolangleys |
| --- | --- |
| 1. 0.25% bis(2,4,6-tri-tert. butylphenyl)phosphite | 105 |
| 2. 0.25% bis(2,4,6-tri-tert. butylphenyl)phosphite + 0.25% n-octadecyl 3,5-di-tert.-butyl-4-hydroxybenzoate | 180 |
| 3. 0.50% 2-(2'-hydroxy-3',5'-di-tertamylphenyl)benzotriazole | 94 |
| 4. 0.50% n-octadecyl 3,5-di-tert-butyl-4-hydroxybenzoate | 106 |
| 5. Blank | 62 |

*Each of the samples tested and the blank contain 0.10 octadecyl-3-(3',5'-di-tert.-butyl-4-hydroxyphenyl) propionate + 0.3% dilaurylthiodipropionate + 0.1% calcium stearate.

The above results show that the hindered phosphite of this invention is particularly effective as a light stabilizer in 5 mil polypropylene monofilament on outdoor aging both as the sole light stabilizer present as well as in combination with another light stabilizer, n-octadecyl-3,5-di-tert-butyl-4-hydroxybenzoate.

EXAMPLE 3

Unstabilized polypropylene powder (Hercules Profax 6501) was thoroughly blended with the indicated amounts of additives (Tables II, III and IV). The blended materials were then milled on a two-roll mill at 182° C. for 5 minutes, after which time the stabilized polypropylene was sheeted from the mill and allowed to cool.

Part of the milled polypropylene sheets were then cut into pieces and compression molded on a hydraulic press at 220° C., 175 psi into 25 mil thick plaques and part into 5 mil thick films.

Testing Methods (a) Rotary Oven-Aging Test

The resulting plaques of 25 mil thickness were tested for resistance to accelerated aging in a rotary oven at 150° C. Specimen colors were determined during the oven aging. When the plaques showed the first signs of decomposition (e.g., cracking or brown edges) they were considered to have failed. The results are shown below in Tables II and III. The amounts of the additives are expressed in weight percent based on the weight of the polymer.

(b) Artificial Light Exposure Test

This test is conducted in an FS/BL unit, basically of the American Cyanamid design, which consists of 40 tubes of alternating fluorescent sunlamps and black lights (20 of each). The 5 mil sample films are mounted on 3"×2" IR card holders with 1¾"×1" windows and are placed on a rotating drum 2 inches from the bulbs in the FS/BL unit. The time in hours is noted for the development of 0.5 carbonyl absorbance units as determined on an Infra-red Spectrophotometer. The development of carbonyl functional groups in the polymer is proportional to the amount of degradation caused by the ultraviolet light exposure.

The test results reported below in Tables III and IV are obtained according to the procedures described above. The amounts of the additives are expressed in weight percent based on the weight of the polymer.

TABLE II

| Additives | Time in Hours to Failure in Rotary Oven Aging | Gardner 0 Hours | Color 100 Hours | On Failure |
|---|---|---|---|---|
| 1. 0.30 bis(2,4,6-tri-tert.-butylphenyl) phosphite + 0.1% tetrakis-[methylene-3-(3',5'-di-tert-butyl-4'-hydroxy-phenyl)propionate]methane | 1105 | 0 | 1 | 3 |
| 2. 0.2% tetrakis-[methylene-3-(3',5'-di-tert-butyl-4-hydroxyphenyl)propionate]methane | 1190 | 0 | 2 | Tan 5 |

TABLE III

| Additives | Time in Hours to Failure in Rotary Oven Aging | Gardner 0 Hours | Color 100 Hours | On Failure | Time in Hours to .5 Carbonyl Absorbance Units |
|---|---|---|---|---|---|
| 1. 0.3% bis-(2,6-di-t-butylphenyl) phosphite + 0.1% tetrakis-[methylene-3-(3',5'-di-tert-butyl-4'-hydroxyphenyl)propionate]methane | 1330 | 0 | 1 | Tan 4 | 420 |
| 2. 0.2% tetrakis-[methylene-3-(3',5'-di'tert-butyl-4'-hydroxyphenyl)propionate] methane | 1185 | 0 | 2 | Tan 4 | 170 |
| 3. 0.1% tetrakis-[methylene-3-(3',5'-di-tert-butyl-4'-hydroxyphenyl)propionate] methane + 0.3% distearylthio-dipropionate | 2160 | 0 | 2 | Tan 5 | 250 |

TABLE IV

| Additives | Time in Hours to 0.5 Carbonyl Absorbance Units |
|---|---|
| 1. 0.5% bis (2,4,6-tri-tert-butylphenyl) phosphite + 0.5% 2-(3',5'-di-tert-butyl-2'-hydroxyphenyl)-5-chlorobenzotriazole + 0.2% di-n-octadecyl-3,5-di-tert-butyl-4-hydroxy benzyl phosphonate | 1965 |
| 2. 0.5% bis (2,4,6-tri-tert-butylphenyl) phosphite + 0.5% 2,4-di-tert-butylphenyl 3,5-di-tert-butyl-4-hydroxybenzoate + 0.2% di-n-octadecyl-3,5-di-tert-butyl-4-hydroxy benzyl phosphonate | 1895 |

The above results show that the phosphites of this invention are good synergists for phenolic antioxidants such as tetrakis-[methylene-3-(3',5'-di-tert-butyl-4'hydroxyphenyl)propionate]methane yielding polypropylene plaques of low color even on failure. While the data shows that formulations containing a phenolic antioxidant and DSTDP experience longer oxidation times to failure than formulations containing phenolic antioxidant and phosphite, the data also shows that the phosphite of the present invention contributes much more to light stability in the presence of a phenolic antioxidant than does DSTDP (Table III).

The results of Table IV show that bis(2,4,6-tri-tert-butylphenyl)phosphite, when used in formulations containing commercial antioxidants, provides good light stabilization.

Comparatively good stabilization is obtained when the concentration of hindered phosphite varies from 0.05% to 1%.

Other hindered phenolic antioxidants may be used in place of tetrakis-[methylene-3-(3',5'-di-tert-butyl-4'-hydroxyphenyl)propionate]methane in the above mentioned compositions with hindered phosphites as, for example, di-n-octadecyl α-(3-t-butyl-4-hydroxy-4-methylbenzyl) malonate, 2,4-bis(n-octylthio)-6-(3,4-di-t-butyl-4-hydroxyaniline)-1,3,5-triazine, octadecyl 3-(3',5'-di-t-butyl-4'-hydroxyphenyl)propionate, di-octadecyl(3,5-di-t-butyl-4-hydroxybenzyl)phosphonate, tris-(3,5-di-t-butyl-4-hydroxybenzyl)isocyanurate, 2,6-di-tert-butyl-4-methylphenol, N,N,N-tris-(3,5-di-tert-butyl-4-hydroxybenzyl)isocyanurate, and 2,4,6-tris(3,5-di-tert-butyl-4-hydroxybenzyl)-1,3,5-trimethylbenzene.

The hindered phosphite composition of Table II is also stabilized when 2(2'-hydroxy-3',5'-di-t-butylphenyl)-5-chlorobenzotriazole is replaced with the following UV absorbers:
(a) 2-hydroxy-4-methoxy-5-sulfobenzophenone trihydrate
(b) 2-hydroxy-4-n-octoxybenzophenone
(c) 2,2'-thiobis(4-t-octylphenolate)-1-n-butylamine nickel II
(d) p-octylphenyl salicylate
(e) 2,2'-dihydroxy-4,4'-dimethoxybenzophenone
(f) 2(2'-hydroxy-5'-methylphenyl)-benzotriazole.

The compositions of Tables II, III and IV are also stabilized when bis(2,4,6-tri-tert-butylphenyl)phosphite and bis(2,6-di-t-butylphenyl)phosphite are replaced with the following phosphites:
(a) bis(2,6-di-t-butyl-4-methylphenyl)phosphite
(b) bis(2,6-di-t-butyl-4-chlorophenyl)phosphite
(c) bis(2,4,6-tri-t-butylphenyl)phosphorochlorodite
(d) bis(2,6-di-t-butyl-4-chlorophenyl)phosphorochlorodite
(e) bis(2,6-di-t-butyl-4-methylphenyl)phosphorochlorodite
(f) bis(2,4,6-tri-α-phenylethyl phenyl)phosphite
(g) bis(2,6-di-t-butyl-4-nonylphenyl)phosphite
(h) bis(2,4,6-tris-isopropylphenyl)phosphite

EXAMPLE 4

Process Stability Test 35 g of unstabilized polypropylene (Hercules Profax 6801) was solvent blended with the indicated amounts of process stabilizers (Table V), using methylene chloride as solvent. After blending, the solvent was removed under vacuum at room temperature.

A Brabender Plasticorder was set up with a jacket temperature setting of 260° C.; shear rate 120 rpm; roller type 6; range X1; booster and control heater setting 240; preload position 0; lever arm setting 1:5; and damper setting 6 seconds.

After the Brabender Plasticorder reached the desired temperature (260° C.) and was maintained there in equilibrium for 10 minutes, the rotor motor was turned on and the rotor speed brought to 120 rpm. The torque recording chart paper was set to the 9.5 minute mark and the chart was turned on.

When the recorder pen tip intersected the zero minute line, the polypropylene formulation was added rapidly to the bowl of the Plasticorder. The Plasticorder was run for 5 minutes under the above conditions with the torque being charted in meter-grams (m-g).

The torque in meter-grams which was recorded after 5 minutes of mixing time is shown below in Table V. Colors of the polypropylene formulations were also determined at the 5 minute point using the Hunter ΔLba system and are shown below in Table V. The higher the torque and the lower the color number the more effective is the stabilizer in preventing the degradation of the polypropylene during the processing operation.

The amounts of the additives are expressed in weight percent based on the weight of the polymer.

TABLE V

| Additives* | TORQUE (meter-gams) | COLOR (ΔLBA) |
|---|---|---|
| 1. 0.05% bis(2,4,6-tri-tert-butyl-phenyl)phosphite | 215 | 22 |
| 2. Blank | 110 | 29 |

*The formulation tested and the blank each contain 0.3% distearylthiodipropionate + 0.1% calcium stearate.

EXAMPLE 5

100 parts of unstabilized high density polyethylene with a molecular weight of ~500,000 (Lupolen 5260 Z, BASF) was mixed thoroughly with the stabilizers mentioned in the table below at the indicated concentrations. The mixtures were kneaded in a Brabender Plasticorder at 200° C. and 50 rpm during 20 minutes. During this time the torque was recorded continuously. The torque remained constant during a period of time which is characteristic of the incorporated stabilizers. After the constant period the torque increased rapidly due to crosslinking of the polymer. The time in minutes of the constant period is shown in the table below.

The amounts of the additives are expressed in weight percent based on the weight polymer.

TABLE VI

| Stabilizers | Time in minutes to increase of torque |
|---|---|
| 1. 0.1% bis(2,4,6-tri-tert-butylphenyl)phosphite | 2 |
| 2. 0.05% tetrakis [methylene-3(3',5'-di-tert-butyl-4'-hydroxyphenyl)propionate] methane | 4 |
| 3. 0.1% bis(2,4,6-tri-tert-butylphenyl)phosphite + 0.05% tetrakis [methylene-3(3',5'-di-tert-butyl-4'-hydroxyphenyl)propionate] methane | 9 |
| 4. Blank | 1½ |

The above data shows that bis(2,4,6-tri-tert-butylphenyl)phosphite acts synergistically in the process-stabilization of high molecular weight polyethylene together with a hindered phenol such as tetrakis[methylene-3(3',5'-di-tert-butyl-4'-hydroxyphenyl)propionate]methane.

EXAMPLE 6

Acrylonitrile-butadiene-styrene terpolymer (Marbon ABS resin) was thoroughly blended with the indicated amounts of additives (Tables VII and VIII, by milling a resin powder/stabilizer solvent blend at 325° F. for 5 mins. 0.5% calcium stearate was added to the basic formulation to aid milling. The milled sheet was compression molded into 125 mil thick plaques, and the plaques were exposed to a Carbon Arc Fadeometer for 100 hours. After exposure, color and notched Izod impact strengths were determined. Individual plaques were also oven aged for 190 hours at 190° F. Colors were determined using the Hunter ΔLba system. The results are shown in Table VII and VIII.

The amounts of the additives were expressed in weight percent based on the weight of the polyemer.

TABLE VII

ABS Resin (Marbon) Oven-Aging
125 mil. Plaques
Discoloration Tendencies

| | ΔLBA After Oven-Aging at 190° F. for | |
|---|---|---|
| Additives* | 0 hrs. | 190 hrs. |
| 1. 0.330% bis(2,4,6-tri-tert.-butylphenyl)phosphite | 1 | 4 |
| 2. 1.657% trinonylphenylphosphite (TNPP) | 2 | 4 |
| 3. Base resin | 0 | 9 |

*Each formulation contains 0.5% calcium stearate

TABLE VIII

ABS Resin (Marbon)
Carbon Arc Fadeometer Exposure of
125 Mil. Plaques
Color and Notched IZOD

| Additives[2] | Original | Color (ΔLBA) After 100 Hrs. CAF[1] Exposure | % Ret. of Impact Strength | % Improvement |
|---|---|---|---|---|
| 1. 0.330% bis(2,4,6-tri-tert.-butylphenyl) phosphite | −2 | −3 | 73 | 43 |
| 2. 1.857% trinonylphenyl-phosphite (TNPP) | −2 | −3 | 63 | 24 |

TABLE VIII-continued

ABS Resin (Marbon)
Carbon Arc Fadeometer Exposure of
125 Mil. Plaques

| Additives[2] | Color and Notched IZOD | | | |
|---|---|---|---|---|
| | Original | Color (ΔLBA) After 100 Hrs. CAF[1] Exposure | % Ret. of Impact Strength | % Improvement |
| 3. 0.085% bis(2,4,-6-tri-tert.-butylphenyl) phosphite + 0.15% 2,2'-methylene-bis(6-t-butyl-4-ethylphenol) | 4 | 0 | 83 | 65 |
| 4. 0.50% trinonylphenyl-phosphite + 0.15% 2,2'-methylene-bis(6,-t-butyl-4-ethylphenol) | 4 | 0 | 70 | 37 |
| 5. Base resin | 0 | −1 | 51 | |

Notes:
[1]CAF = Carbon Arc Fadeometer
[2]Each formulation contains 0.5% calcium stearate The results in Tables VII and VIII show that the hindered phosphite bis(2,4,6-tri-tert.-butylphenyl)-phosphite provides equal stabilization of ABS resin against degradation by heat and light as demonstrated by resistance to discoloration and retention of impact strength at a concentration about one fifth that of TNPP. It can, therefore, be concluded that the phosphite of this invention is about 5.5 times as efficient as the prior art compound TNPP as a light stabilizer for ABS resin.

Table VIII also shows that bis(2,4,6-tri-tert.-butylphenyl)phosphite is similarly superior to the prior art compound TNPP when used in ABS resin with a phenolic antioxidant such as 2,2'-methylene-bis(6-t-butyl-4-ethylphenol).

The compositions of Tables VII and VIII are also stabilized with bis(2,4,6-tri-tert.-butylphenyl)phosphite is replaced with the following phosphites:
(a) bis(2,6-di-t-butyl-4-chlorophenyl)phosphite
(b) bis(2,4,6-tri-t-butylphenyl)phosphorochloridite
(c) bis(2,4,6-tri-α-phenylethyl phenyl)phosphite
(d) bis(2,6-di-t-butyl-4-nonylphenyl)phosphite

EXAMPLE 7

Impact polystyrene (TMDH 5161—Union Carbide) was thoroughly blended with the indicated amounts of additives (Table IX) by milling a resin/stabilizer blend at 127° C. for five minutes. 0.02% zinc stearate #44 (Witco) was added to the basic formulation to aid milling. The milled sheet was compression molded into 20 mil thick plaques at 400° F. for 5 minutes. Specimens were die cut from the plaques and oven aged in a forced draft oven at 80° C. Specimen colors were determined during the oven aging. The results are shown below in Table IX. The amount of the additives are expressed in weight percent based on the weight of the polymer.

TABLE IX

Stabilization of Impact Polystyrene
20 mil. plaques

| Additives* | Gardner Color After Oven-Aging at 80° C. for Hours | | | |
|---|---|---|---|---|
| | 0 | 675 | 1400 | 2300 |
| 1. 0.1% bis(2,4,6-tri-tert.-butylphenyl)phosphite + 0.3% 2,6-di-t-butyl-4-methyl-phenol (BHT) | 1 | 1 | 2 | 4 |

TABLE IX-continued

Stabilization of Impact Polystyrene
20 mil. plaques

| Additives* | Gardner Color After Oven-Aging at 80° C. for Hours | | | |
|---|---|---|---|---|
| | 0 | 675 | 1400 | 2300 |
| 2. 0.2% trinonylphenylphosphite + 0.3% BHT | 2 | 3 | 5 | 5 |
| 3. 0.1% bis(2,4,6-tri-tert.butyl-phenyl)phosphite + 0.1% octa-decyl-3-(3', 5'-di-tert.-butyl-4'-hydroxyphenyl)propionate | 1 | 1 | 3 | 5 |
| 4. 0.2% trinonylphenylphosphite + 0.1% octadecyl-3-(3',5'-di-tert.-butyl-4'-hydroxyphenyl) propionate | 2 | 3 | 5 | 5 |
| 5. Base resin | 1 | 6 | 9 | 11 |

*Each formulation contains 0.02% zinc stearate.

The results in Table IX show that impact polystyrene formulations containing bis(2,4,6-tri-tert.-butylphenyl)-phosphite are more resistant to discoloration then those containing trinonylphenylphosphite, in the presence of phenolic antioxidants.

The compositions of Table IX are also stabilized when bis(2,4,6-tri-tert.-butylphenyl)phosphite is replaced with the following phosphites:
(a) bis(2,6-di-t-butyl-4-methylphenyl)phosphite
(b) bis(2,6-di-t-butyl-4-chlorophenyl)phosphite
(c) bis(2,4,6-tri-t-butylphenyl)phosphorochloridite
(d) bis(2,6-di-t-butyl-4-nonylphenyl)phosphite

EXAMPLE 8

A. A quantity of SBR emulsion containing 100 g. of rubber (500 ml of 20% SBR obtained from Texas U.S. Synpol 1500), previously stored under nitrogen, is placed in a beaker and a resin acid salt emulsion of the indicated amount of additive in Table X is added and the composition is stirred vigorously. The pH of the emulsion is adjusted to 10.5 with an 0.5 N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber composition is isolated by filtration through cheese cloth, and rinsed with distilled water. After three subsequent washings with fresh distilled water, the coagulated rubber is dried, first at 25 mm Hg and finally to constant weight under high vacuum (>1 mm) at 40°–45° C. The resultant formulation is compression molded at 125° C. into 25 mil plaques.

B. Gel Content and Color Development Method

The 25 mil thick compression molded plaques from the above coagulated rubber are oven aged at 100° C. in a forced draft oven. Toluene insoluble gel measurements and Gardner colors are taken periodically. The % gel content in the sample is calculated using the following expression:

$$\% \text{ Gel} = 100 \frac{(W_1 - 10W_f)}{W_1}$$

where $W_1$ is the weight of sample in 100 ml. toluene at room temperature and $W_f$ is the weight of residue in 10 ml. filtered solution after evaporation of solvent at 80° C. The amount of the additive is expressed in weight percent based on the weight of the polymer.

TABLE X

| Additive | Hours to Onset of Gel | Gardner Color After Hours | | | |
|---|---|---|---|---|---|
| | | 0 | 20 | 70 | 120 |
| 0.5% bis(2,4,6-tri-tert.-butylphenyl)phosphite | 42 | 0 | 4 | 5 | 9 |
| Base resin | 10 | 0 | 5 | 9 | — |

EXAMPLE 9

A rosin acid salt emulsion of the indicated amount of stabilizer in Table XI was added to SBR latex (Part A, 300 gm.) with stirring. To this mixture 27.03 gm Part B and 6170 gm. Part C were added very slowly and the mixture was stirred vigorously for two minutes followed by slow stirring for one minute. The resulting foam was poured onto jute between two 3/16" metal bars 10" apart and was leveled by means of a doctor blade. The resulting foam on the jute was cured at 260° F. for 45 minutes. The 2"×2" samples of cured foamed latex (5/16" thick on jute) were exposed to oven (270° F.) and to the Carbon Arc Fadeometer. After exposure, specimen colors were determined using the Hunter ΔLba system and hours to embrittlement were determined. Embrittlement was determined by bending the specimen back upon itself until the jute side was touched. The oven aged samples were allowed to cool at least one-half hour before flexing.

Part A: Latex
Part B: Filler supplied by TR+C
Part C: NH₄OH+Vulcanizing agent

The amount of the additive is expressed in weight percent based on the weight of the polymer.

TABLE XI

| Additive | Hours to Embrittlement | Hunter (L-b) Color After Hours Exposure | | | |
|---|---|---|---|---|---|
| | | 0 | 10 | 20 | 30 |
| 0.125% bis(2,4,6-tri-tert.-butylphenyl) Phosphite | 10 | 77.0 | 41.1 | 33.0 | 29.4 |
| Base resin | 5 | 77.9 | 38.8 | 30.1 | 26.1 |

The results of Examples 8 and 9 show that the hindered phosphites of the invention are effective stabilizers of emulsion SBR and SBR latex foam.

EXAMPLE 10

Unstabilized linear polyethylene is solvent blended in methylene chloride with 0.5% by weight of the substrate of bis(2,6-di-t-butyl-4-methylphenyl)phosphite and then vacuum dried. The resin is then extrusion compounded on a 1 inch 24/1=L/D extruder, melt temperature 450° F. (232° C.) and pressed for 7 minutes at a temperature of 163° C. and a pressure of 2000 psi into a sheet of uniform thickness of 100 mil. The sheets are then cut into plaques of 2"×2". The plaques are then exposed in an FS/BL exposure device and color measurements made periodically using a Hunter Color Difference Meter Model D25. Polyethylene stabilized with the above compound is found to be much more stable than the unstabilized polyethylene or the polyethylene stabilized only with an antioxidant.

EXAMPLE 11

To 50 g. of polyacetal resin containing 0.1% of an acid scavenger, dicyandiamide, is added 0.2% by weight of bis(2,6-di-t-butyl-4-chlorophenyl)phosphite and the composition is milled for 7 minutes at 200° C. in a Brabender Plasti-recorder. The milled formulation is subsequently pressed into a 40 mil sheet at 215° C. at 350 psi for 90 seconds then cooled quickly in the cold press at 350 psi. The stabilized sheets are then remolded for 2 minutes at contact pressure and for 3 minutes at 300 psi at 215° C. to give plaques 1½"×2¼"×125 mil. Thereafter, the testing procedure of Example 10, 3b is followed to determine the light stability of the samples. The stabilized samples are found to be much more stable than the unstabilized samples.

EXAMPLE 12

Unstabilized thoroughly dried polyethylene terephthalate chips are dry blended with 1.0% of bis(2,6-di-t-butyl-4-methylphenyl)phosphorochloridite. 60/10 denier multifilament is melt spun at a melt temperature of 209° C. The oriented fiber is wound on white cards and exposed in an Xenon Arc Fadeometer. Color measurements are made periodically with a Hunter Color Difference Meter Model D25. The stabilized samples are found to be much more light stable than the unstabilized samples.

EXAMPLE 13

(a) A composition comprising acrylonitrilebutadienestyrene terpolymer and 1% by weight of bis(2,6-di-t-butyl-4-nonylphenyl)phosphite resists embrittlement due to exposure to ultraviolet light longer than one which does not contain the stabilizer.

(b) A composition comprising polyurethane prepared from toluene diisocyanate and alkylene polyols and 1.0% by weight of bis(2,6-di-t-butyl-4-methylphenyl)-phosphorochloridite is more stable to sunlight, fluorescent sunlamps, black lights and fluorescent lights than the unformulated polyurethane.

(c) A composition comprising a polycarbonate prepared from bisphenol-A and phosgene and 1% by weight of bis(2,4,6-tri-α-phenylethyl phenyl)phosphite resists discoloration due to exposure to ultraviolet light longer than one which does not contain the stabilizer.

(d) A composition comprising polymethylmethacrylate and 0.25% by weight of bis(2,4,6-tri-tert.-butylphenyl)phosphite resists discoloration due to exposure to ultraviolet light longer than one which does not contain the stabilizer.

EXAMPLE 14

(a) A stabilized polyamide (nylon 6,6) is prepared by incorporating therein 0.1% of bis(2,6-di-t-butylphenyl)-phosphite. The light stability of the stabilized composition is superior to that of an unstabilized polyamide.

(b) A stabilized polyphenylene oxide polymer (prepared by polymerizing 2,6-dimethylphenol is prepared by incorporating therein 0.5% by weight of bis(2,6-di-t-butyl-4-chlorophenyl)phosphorochloridite. The stabilized compositions resist embrittlement due to exposure to ultraviolet light longer than one which does not contain the stabilizer.

(c) A stabilized crystalline polystyrene is prepared by incorporating therein 0.1% by weight of the bis(2,6-di-t-butyl-4-methylphenyl)phosphorochloridite. The stabilized composition resists embrittlement due to exposure to ultraviolet light longer than one which does not contain the stabilizer.

EXAMPLE 15

The indicated amounts of additives (Table XII) were blended with dried Celanex 3300 (30% glass reinforced polybutylene terephthalate), and then extruder compounded at a melt temperature of 465° F. Tensile test specimen were prepared by injection molding.

Aging of the tensile test specimens was conducted in a forced draft air oven at 185° C. The specimens were tested for percent retention of initial tensile in the Instron Tensile Testing Apparatus (Instron Engineering Corporation, Quincy, Massachusetts). The test results are reported in the following table. The amounts of the additives are expressed in weight percent based on weight of the polymer.

TABLE XII

| Additives | Oven Aging at 185° C. % Retention of Initial Tensile | | | |
|---|---|---|---|---|
| | 4 weeks | 8 weeks | 11 weeks | 12 weeks |
| 0.5% di-n-octadecyl-3,5-di-tert-butyl-4-hydroxy-benzyl-phosphonate | 91 | 56 | 35 | 39 |
| 0.5% bis-(2,4,6-tri-t-butyl-phenyl)phosphite | 112 | 62 | 55 | 48 |
| 0.25% di-n-octadecyl-3,5-di-tert-butyl-4-hydroxy-benzyl-phosphonate + 0.25% bis(2,4,6-tri-t-butyl-phenyl)phosphite | 112 | 63 | 38 | 45 |
| 0.5% N,N'-hexamethylene bis (3,5-di-tert-butyl-4-hydroxy-hydro-cinnamamide | 88 | 49 | 38 | 34 |
| 0.25% N,N'-hexamethylene bis (3,5-di-tert-butyl-4-hydroxy-hydro-cinnamamide) + 0.25% bis-(2,4,6-tri-t-butylphenyl) | | | | |

TABLE XII-continued

| Additives | Oven Aging at 185° C. % Retention of Initial Tensile | | | |
|---|---|---|---|---|
| | 4 weeks | 8 weeks | 11 weeks | 12 weeks |
| phosphite | 97 | 62 | 45 | 43 |
| Blank | 70 | 36 | 25 | 24 |

What is claimed is:

1. Compositions comprising a polymer normally subject to deterioration stabilized with
  (a) 0.005 to 5% of a stabilizer having the formula

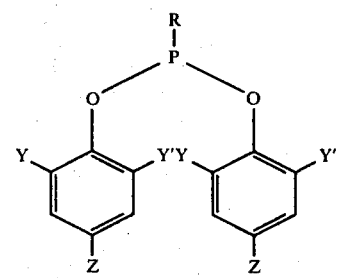

wherein
R is hydroxy or chlorine,
Y and Y' are independently alkyl having from 1 to 12 carbon atoms or aralkyl having from 7 to 12 carbon atoms, and
Z is independently hydrogen, halogen, alkyl having from 1 to 12 carbon atoms or aralkyl having from 7 to 12 carbon atoms.

2. A composition according to claim 1 wherein R is hydroxy.

3. A composition according to claim 1 wherein R is chlorine.

4. A composition according to claim 1 wherein Y and Y' are each t-butyl.

5. A composition according to claim 1 wherein R is hydroxy,
Y and Y' are each t-butyl, and
Z is hydrogen or t-butyl.

6. A composition according to claim 1 wherein the polymer is polyolefin.

7. A composition according to claim 1 wherein the polymer is polypropylene.

8. A composition according to claim 1 wherein the polymer is acrylonitrile-butadiene-styrene terpolymer.

9. A composition according to claim 1 wherein the polymer is polystyrene.

10. A composition according to claim 1 wherein the polymer is styrene-butadiene copolymer.

11. A composition according to claim 1 wherein the polymer is a polyester composition containing polyalkylene terephthalate.

12. A composition according to claim 1 wherein the polymer is selected from polypropylene, polyethylene, acrylonitrile-butadiene-styrene terpolymer, styrene-butadiene copolymer, polyalkylene terrphthalate and impact polystyrene.

13. The composition according to claim 1 which contains 0.005 to 5% of a thioco-stabilizer.

14. A composition according to claim 13 comprising
  (i) from 0.005 to 5% of the hindered phosphite of formula (I) and from 0.005 to 5% of the thio-costabilizer and (ii) a polymer selected from acrylonitrile-butadiene-styrene terpolymer, styrene-butadiene copolymer, and polyalkylene terephthalate.

15. The composition according to claim 1 which contains 0.005 to 5% of a phenolic antioxidant.

16. A composition according to claim 15 consisting essentially of
(i) a polymer selected from polypropylene, polyethylene, impact polystyrene, polyalkylene terephthalate and acrylonitrile-butadiene-styrene terpolymer,
(ii) a hindered phosphite of formula (I), and
(iii) 0.005 to 5% of a phenolic antioxidant selected from tetrakis [methylene 3-(3',5'-di-tert-butyl-4'-hydroxyphenyl)propionate]methane, octadecyl 3-(3'-5'-di-tert-butyl-4'-hydroxyphenyl)propionate, di-n-octadecyl-3,5-di-tert-butyl-4-hydroxybenzyl phosphonate, N,N'-hexamethylene bis(3,5-di-tert-butyl-4-hydroxy-hydrocinnamamide, 2,2'-methylene-bis(6-t-butyl-4-ethylphenol) and 2,6-di-t-butyl-4-methylphenol.

17. A composition according to claim 15 consisting essentially of
(i) polyolefin,
(ii) a hindered phosphite of formula (I), and
(iii) 0.005 to 5% of a thio-co-stabilizer having the formula

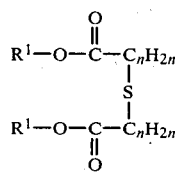

wherein $R^1$ is an alkyl group having from 6 to 24 carbon atoms and n is an integer of from 1 to 6.

18. The composition according to claim 15 which contains 0.005 to 5% of a UV absorber or light stabilizer.

19. A composition according to claim 18 consisting essentially of
(i) polyolefin,
(ii) a hindered phosphite of formula (I)
(iii) 0.005 to 5% of a p-hydroxybenzoate having the formula

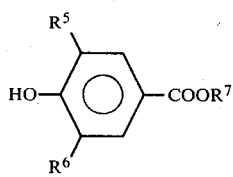

wherein
$R^5$ is (lower) alkyl containing from 1 to 6 carbon atoms,
$R^6$ is hydrogen or (lower) alkyl containing from 1 to 6 carbon atoms, and
$R^7$ is alkyl of from 1 to 24 carbon atoms, phenyl or phenyl substituted by one or two alkyl groups of 1 to 12 carbon atoms, and
(iv) 0.005 to 5% of a phenolic antioxidant selected from tetrakis[methylene 3-(3',5'-di-tert-butyl-4'-hydroxyphenyl)propionate]methane, octadecyl 3-(3',5'-di-tert-butyl-4'-hydroxyphenyl)propionate, di-n-octadecyl-3,5-di-tert-butyl-4-hydroxybenzyl phosphonate, 2,6-di-t-butyl-4-methylphenol, and tris 2,4,6-(3,5-di-t-butyl-4-hydroxybenzyl)isocyanurate.

20. A composition according to claim 18 consisting essentially of
(i) polypropylene,
(ii) a hindered phosphite of formula (I),
(iii) 0.005 to 5% of a benzotriazole having the formula

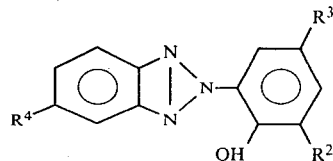

wherein
$R^2$ is hydrogen, chlorine or lower alkyl containing from 1 to 6 carbon atoms,
$R^3$ is hydrogen, alkyl containing 1 to 12 carbon atoms, phenyl or benzyl, and
$R^4$ is hydrogen, chlorine or (lower) alkyl containing from 1 to 6 carbon atoms, and
(iv) 0.005 to 5% of a phenolic antioxidant selected from tetrakis[methylene-3-(3',5'-di-tert-butyl-4'-hydroxyphenyl)propionate]methane, octadecyl 3-(3',5'-di-tert-butyl-4'-hydroxyphenyl)propionate, di-n-octadecyl-3,5-di-tert-butyl-4-hydroxybenzyl phosphonate, 2,6-di-t-butyl-4-methylphenol, and tris-2,4,6-(3,5-di-t-butyl-4-hydroxybenzyl)isocyanurate.

21. The composition according to claim 1 which contains 0.005 to 5% of a UV absorber or light stabilizer.

22. The composition according to claim 15 which contains 0.005 to 5% of a thio co-stabilizer.

23. The composition according to claim 13 which contains 0.005 to 5% of a UV absorber or light stabilizer.

24. The composition according to claim 22 which contains 0.005 to 5% of a UV absorber or light stabilizer.

25. The composition according to claim 19 which contains 0.005 to 5% of a thio-co-stabilizer having the formula

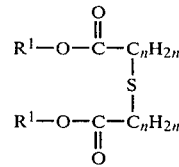

wherein $R^1$ is an alkyl group having from 6 to 24 carbon atoms and n is an integer of from 1 to 6.

26. The composition according to claim 20 which contains 0.005 to 5% of a thio-co-stabilizer having the formula

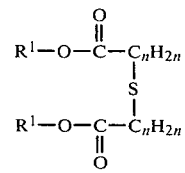

wherein $R^1$ is an alkyl group having from 6 to 24 carbon atoms and n is an integer from 1 to 6.

* * * * *